United States Patent
Sartor et al.

(10) Patent No.: US 11,246,644 B2
(45) Date of Patent: Feb. 15, 2022

(54) SURFACE ABLATION USING BIPOLAR RF ELECTRODE

(71) Applicant: COVIDIEN LP, Mansfield, MA (US)

(72) Inventors: Joe D. Sartor, Longmont, CO (US); Arlen K. Ward, Centennial, CO (US); John A. Hammerland, III, Arvada, CO (US); Eric J. Larson, Broomfield, CO (US); Patrick J. Digmann, Louisville, CO (US)

(73) Assignee: Covidien LP, Mansfield, MA (US)

( * ) Notice: Subject to any disclaimer, the term of this patent is extended or adjusted under 35 U.S.C. 154(b) by 395 days.

(21) Appl. No.: 16/356,230

(22) Filed: Mar. 18, 2019

(65) Prior Publication Data
US 2019/0307501 A1    Oct. 10, 2019

Related U.S. Application Data

(60) Provisional application No. 62/652,954, filed on Apr. 5, 2018.

(51) Int. Cl.
| | |
|---|---|
| *A61B 18/14* | (2006.01) |
| *A61B 18/12* | (2006.01) |
| *A61B 18/00* | (2006.01) |

(52) U.S. Cl.
CPC .......... *A61B 18/14* (2013.01); *A61B 18/1206* (2013.01); *A61B 2018/00559* (2013.01); *A61B 2018/00577* (2013.01); *A61B 2018/142* (2013.01)

(58) Field of Classification Search
CPC . A61B 18/1206; A61B 18/14; A61B 18/1485; A61B 2018/0016; A61B 2018/00559; A61B 2018/00577; A61B 2018/126; A61B 2018/142; A61B 2018/1435
See application file for complete search history.

(56) References Cited

U.S. PATENT DOCUMENTS

| | | | |
|---|---|---|---|
| 552,832 A | 1/1896 | Fort | |
| 4,011,872 A | 3/1977 | Komiya | |
| 4,311,154 A | 1/1982 | Sterzer et al. | |
| 4,532,924 A * | 8/1985 | Auth ............... | A61B 18/14 606/50 |
| 4,565,200 A | 1/1986 | Cosman | |

(Continued)

FOREIGN PATENT DOCUMENTS

| | | |
|---|---|---|
| DE | 39433213 T2 | 5/2004 |
| EP | 1024761 A2 | 8/2000 |

(Continued)

*Primary Examiner* — Michael F Peffley
(74) *Attorney, Agent, or Firm* — Carter, DeLuca & Farrell LLP

(57) ABSTRACT

A surface ablation system includes an electrosurgical generator, and elongated shaft, a plug, and a circuit assembly. The elongated shaft includes a proximal end portion and a distal end portion. The plug is supported on the distal end portion of the elongated shaft. The circuit assembly is supported on the plug and in electrical communication with the electrosurgical generator. The circuit assembly includes spaced-apart traces positioned in arrays about the plug. Each of the traces is configured to emit electrosurgical energy along the arrays to treat tissue positioned adjacent to the traces.

12 Claims, 6 Drawing Sheets

(56) References Cited

U.S. PATENT DOCUMENTS

| | | |
|---|---|---|
| 4,640,298 A | 2/1987 | Pless et al. |
| 4,873,996 A * | 10/1989 | Maurer ................. A61F 2/005 607/138 |
| 4,895,138 A | 1/1990 | Yabe |
| 4,907,589 A | 3/1990 | Cosman |
| 4,998,539 A | 3/1991 | Delsanti |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,100,423 A | 3/1992 | Fearnot |
| 5,160,334 A | 11/1992 | Billings et al. |
| 5,190,541 A | 3/1993 | Abele et al. |
| 5,197,963 A | 3/1993 | Parins |
| 5,197,964 A | 3/1993 | Parins |
| 5,275,162 A | 1/1994 | Edwards et al. |
| 5,275,169 A | 1/1994 | Afromowitz et al. |
| 5,277,201 A * | 1/1994 | Stern ................. A61B 18/14 606/32 |
| 5,281,216 A | 1/1994 | Klicek |
| 5,281,217 A | 1/1994 | Edwards et al. |
| 5,281,218 A | 1/1994 | Imran |
| 5,292,321 A | 3/1994 | Lee |
| 5,293,869 A | 3/1994 | Edwards et al. |
| 5,383,874 A | 1/1995 | Jackson et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,310 A | 4/1995 | Fischer |
| 5,462,545 A | 10/1995 | Wang et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,591,195 A | 1/1997 | Taheri et al. |
| 5,599,345 A | 2/1997 | Edwards et al. |
| 5,609,151 A | 3/1997 | Mulier et al. |
| 5,709,224 A | 1/1998 | Behl et al. |
| 5,713,942 A | 2/1998 | Stern et al. |
| 5,716,410 A | 2/1998 | Wang et al. |
| 5,720,293 A | 2/1998 | Quinn et al. |
| 5,730,128 A | 3/1998 | Pomeranz et al. |
| 5,732,698 A | 3/1998 | Swanson et al. |
| 5,840,077 A | 11/1998 | Rowden et al. |
| 5,860,974 A | 1/1999 | Abele |
| 5,861,036 A | 1/1999 | Godin |
| 5,863,291 A | 1/1999 | Schaer |
| 5,871,483 A | 2/1999 | Jackson et al. |
| 5,876,340 A | 3/1999 | Tu et al. |
| 5,888,743 A | 3/1999 | Das |
| 5,913,854 A | 6/1999 | Maguire et al. |
| 5,951,550 A | 9/1999 | Shirley et al. |
| 6,010,511 A | 1/2000 | Murphy |
| 6,012,457 A | 1/2000 | Lesh |
| 6,016,437 A | 1/2000 | Tu et al. |
| 6,023,638 A | 2/2000 | Swanson |
| 6,027,499 A | 2/2000 | Johnston et al. |
| 6,033,397 A | 3/2000 | Laufer et al. |
| 6,039,701 A | 3/2000 | Sliwa et al. |
| 6,071,283 A | 6/2000 | Nardella et al. |
| 6,080,152 A | 6/2000 | Nardella et al. |
| 6,164,283 A | 12/2000 | Lesh |
| 6,179,836 B1 | 1/2001 | Eggers et al. |
| 6,182,666 B1 | 2/2001 | Dobak, III |
| 6,183,468 B1 | 2/2001 | Swanson et al. |
| 6,197,022 B1 | 3/2001 | Baker |
| 6,338,726 B1 | 1/2002 | Edwards et al. |
| 6,355,031 B1 | 3/2002 | Edwards et al. |
| 6,355,032 B1 | 3/2002 | Hovda et al. |
| 6,358,245 B1 | 3/2002 | Edwards et al. |
| 6,514,246 B1 | 2/2003 | Swanson et al. |
| 6,514,249 B1 | 2/2003 | Maguire et al. |
| 6,673,070 B2 | 1/2004 | Edwards et al. |
| 6,682,528 B2 | 1/2004 | Frazier et al. |
| 6,689,130 B2 | 2/2004 | Arai et al. |
| 6,695,764 B2 | 2/2004 | Silverman et al. |
| 6,712,074 B2 | 3/2004 | Edwards et al. |
| 6,813,520 B2 * | 11/2004 | Truckai ............. A61B 18/1485 600/372 |
| 6,837,886 B2 | 1/2005 | Collins et al. |
| 6,840,935 B2 | 1/2005 | Lee |
| 6,846,312 B2 | 1/2005 | Edwards et al. |
| 6,929,642 B2 | 8/2005 | Xiao et al. |
| 6,994,704 B2 | 2/2006 | Qin et al. |
| 7,004,938 B2 | 2/2006 | Ormsby et al. |
| 7,160,294 B2 | 1/2007 | Croft |
| 7,165,551 B2 | 1/2007 | Edwards et al. |
| 7,179,257 B2 | 2/2007 | West et al. |
| 7,311,708 B2 * | 12/2007 | McClurken ........ A61B 18/1492 606/50 |
| 7,325,546 B2 | 2/2008 | Burbank et al. |
| 7,326,207 B2 * | 2/2008 | Edwards ............ A61B 18/1492 606/41 |
| 7,329,254 B2 | 2/2008 | West et al. |
| 7,371,231 B2 | 5/2008 | Rioux et al. |
| 7,678,106 B2 | 3/2010 | Lee |
| 7,731,712 B2 | 6/2010 | Sampson et al. |
| 10,610,294 B2 * | 4/2020 | Ben-Ezra ............. A61M 19/00 |
| 2002/0161363 A1 | 10/2002 | Fodor et al. |
| 2002/0188242 A1 | 12/2002 | Wu |
| 2003/0028227 A1 | 2/2003 | Neuberger et al. |
| 2004/0249243 A1 | 12/2004 | Kleiner |
| 2005/0010162 A1 | 1/2005 | Utley et al. |
| 2005/0033271 A1 | 2/2005 | Qin et al. |
| 2006/0009758 A1 | 1/2006 | Edwards et al. |
| 2006/0015162 A1 | 1/2006 | Edward et al. |
| 2006/0041256 A1 | 2/2006 | Edwards et al. |
| 2006/0199999 A1 | 9/2006 | Ikeda et al. |
| 2007/0027449 A1 | 2/2007 | Godara et al. |
| 2007/0100335 A1 | 5/2007 | Fischer |
| 2007/0239011 A1 | 10/2007 | Lau et al. |
| 2007/0276286 A1 | 11/2007 | Miller |
| 2008/0051882 A1 | 2/2008 | Rubin |
| 2008/0065003 A1 | 3/2008 | Neuberger et al. |
| 2008/0071269 A1 | 3/2008 | Hilario et al. |
| 2009/0012512 A1 | 1/2009 | Utley et al. |
| 2009/0012513 A1 | 1/2009 | Utley et al. |
| 2009/0012518 A1 | 1/2009 | Utley et al. |
| 2009/0318914 A1 * | 12/2009 | Utley ................. A61B 18/1485 606/33 |
| 2014/0378965 A1 | 12/2014 | Atwell |
| 2016/0121112 A1 * | 5/2016 | Azar .................. A61N 1/0512 601/2 |

FOREIGN PATENT DOCUMENTS

| | | |
|---|---|---|
| GB | 2347083 B | 6/2001 |
| GB | 2434545 A | 8/2007 |
| WO | 2007143281 A2 | 12/2007 |

* cited by examiner

SURFACE ABLATION USING BIPOLAR RF ELECTRODE

CROSS REFERENCE TO RELATED APPLICATIONS

This application claims the benefit of U.S. Provisional Patent Application No. 62/652,954, filed Apr. 5, 2018, the entire contents of which are incorporated by reference herein.

TECHNICAL FIELD

The present disclosure relates to ablation devices, systems, and/or methods for treating tissue. More specifically, the present disclosure relates to cervical ablation devices for treating uterine cervical tissue.

BACKGROUND

Cervical cancer is the fourth most common cancer in women worldwide. Approximately 260 thousand annual deaths are preventable with early detection and treatment. Early detection can be effectuated by visual inspection with Acetic Acid (VIA) or a Pap smear. Currently more than 1 million procedures are performed annually in the developed world to treat cervical cancer. With an easy treatment procedure and VIA, approximately double the amount of procedures could be effectuated globally.

Current treatments include conization excision and ablative therapies. Conization excision requires a well-trained practitioner and may involve intra-op and/or post-op bleeding. With conization excision, there is also increased risk of preterm birth. Ablative therapies may include cryotherapy, thermal-chemical, diathermy, or laser. While cryotherapy and chemical therapy may be easy to perform, such procedures can involve intraoperative pain and cramping as well as slow recovery with vaginal discharge. Further, existing treatments can be long and painful for patients in an ambulatory setting without anesthesia. Even with these treatments, there is still 3-5 percent recurrence at 12 months.

SUMMARY

Accordingly, a need exists to provide an easy treatment with reduced risks of patient pain and discomfort that can be effectuated globally.

In accordance with one aspect of the disclosure, a surface ablation system includes an electrosurgical generator, an elongated shaft including a proximal end portion and a distal end portion, a plug supported on the distal end portion of the elongated shaft, and a circuit assembly supported on the plug and in electrical communication with the electrosurgical generator. The circuit assembly includes a plurality of spaced-apart traces positioned in arrays about the plug. Each of the traces is configured to emit electrosurgical energy along the arrays to treat tissue positioned adjacent to the traces.

In embodiments, the traces may be positioned to achieve a specific depth of tissue thermal necrosis. The specific depth may be about 1 mm.

In some embodiments, the traces may be configured to effectuate a secondary thermal necrosis in tissue irregularities not in direct contact with the traces.

According to yet another aspect of the disclosure, a method for effectuating surface ablation is provided. The method includes conducting electrosurgical energy through a plurality of spaced-apart traces positioned in arrays about a distal end portion of an elongated shaft to ablate tissue and effectuating secondary thermal necrosis in tissue irregularities not in direct contact with the traces.

Effectuating secondary thermal necrosis may be achieved by one of:

electrical communication between traces adjacent to an electrically conductive tissue that lines the irregularities, electrical communication between the traces and fluid contained within the irregularities, heat transferred from a primary heating area as steam or thermally charged fluid from an electrode array contact area defined by the traces, or continued electrical driven effect through electrically conductive fluid discharged from a primary contact area into the irregularity.

The method may involve causing power shutoff of the electrosurgical energy based on a sharp, sustained impedance rise following a previous minimum value.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
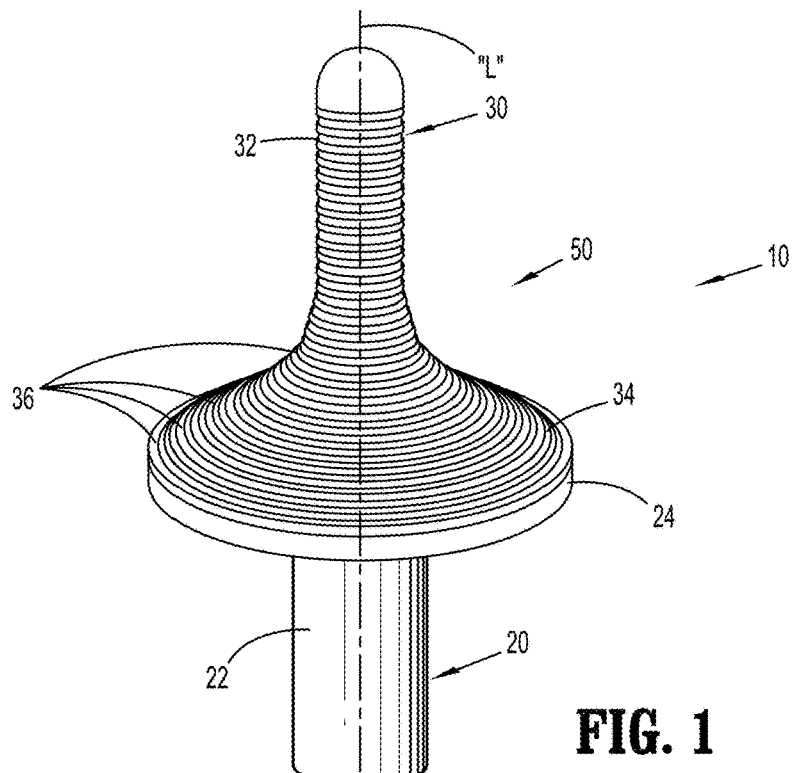
FIG. 1 is a perspective view of a surface ablation system in accordance with the principles of the present disclosure.

Embodiments of the presently disclosed devices are described in detail with reference to the drawings, in which like reference numerals designate identical or corresponding elements in each of the several views. As used herein, the term "distal" or "leading" refers to that portion of the device that is farther from the user, while the term "proximal" or "trailing" refers to that portion of the device that is closer to the user.

Figure 2:
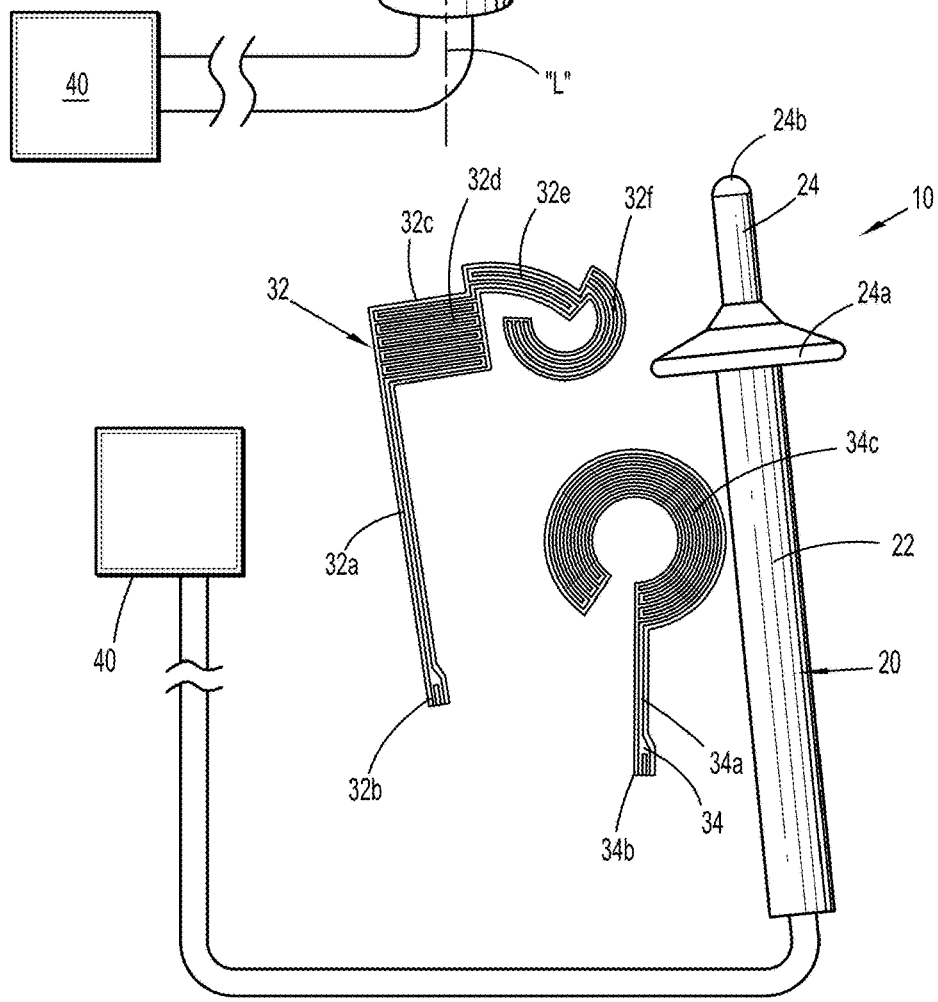
FIG. 2 is a perspective view, with parts separated, of the surface ablation system of FIG. 1.

Referring to FIGS. 1 and 2, a surface ablation system, generally referred to as 10, defines a longitudinal axis "L-L" and includes a shaft assembly 20, a circuit assembly 30 supported on the shaft assembly 20, and an electrosurgical generator 40 disposed in electrical communication with the circuit assembly 30. The surface ablation system 10 may be configured to use bipolar RF energy. Although any suitable electrosurgical generator may be utilized, for a more detailed description of one example of such an electrosurgical generator, reference can be made to U.S. Pat. No. 8,784,410, the entire contents of which are incorporated by reference herein.

The shaft assembly 20 of the surface ablation system 10 includes an elongated shaft 22 that extends distally to a plug portion 24. The plug portion 24 includes an annular flange 24a on a proximal end portion of the plug portion 24, and a blunt tip 24b at a distal end portion of the plug portion 24. The annular flange 24a may have a conical configuration.

The circuit assembly 30 of the surface ablation system 10 includes a first flex circuit 32 and a second flex circuit 34 that are mountable to the plug portion 24 and configured to electrically communicate with the electrosurgical generator 40. The first and/or second flex circuits 32, 34 may include any suitable flexible material.

The first flex circuit 32 of the circuit assembly 30 includes a strip 32a having a foot 32b at a first end portion of the strip 32a, and an arm assembly 32c at a second end portion of the strip 32a. The arm assembly 32c includes a tab 32d coupled to the strip 32a, first arm 32e extending from the tab 32d, and a second arm 32f extending from the first arm 32e. The first arm 32e may be cantilevered to a distal portion of the tab 32d (e.g., a distal corner of the tab 32d at a free end of the tab 32d). The second arm 32f may be cantilevered to a distal portion of the first arm 32e (e.g., a corner of the distal portion of the first arm 32e). The first arm 32e, the second arm 32f, and/or the tab 32d may have any suitable shape and/or configuration. In some embodiments, the first and/or second arms 32e, 32f may include linear and/or curvilinear configurations. In certain embodiments, the tab 32d may have a rectangular or flag-shaped configuration.

The second flex circuit 34 of the circuit assembly 30 includes a strip 34a having a foot 34b at a first end portion of the strip 34a, and an arm 34c at a second end portion of the strip 34a. The arm 34c may be cantilevered to the second end portion of the strip 34a. The arm 34c may have suitable configuration such as an annular or arcuate configuration.

Each of the first and second flex circuits 32, 34, and the respective components thereof may be flexibly movable relative to on another to enable the first and/or second flex circuits 32, 34 to be positioned and/or wrapped about the plug portion 24 of the shaft assembly 20 as seen in FIG. 2. One or both of the first and second flex circuits 32, 34 may include one or more traces 36 that are configured to conduct electrosurgical energy for treating tissue. The traces 36 may be positioned in one or more arrays about the plug portion 24. The one or more arrays may be radially and/or axially spaced apart relative to the longitudinal axis "L-L" of the surface ablation system 10.

With the first and second flex circuits 32, 34 of the circuit assembly 30 mounted to the plug portion 24 of the shaft assembly 20, the plug portion 24 and the first and second flex circuits 32, 34 (and the components thereof) define an end effector electrode 50 that may be configured to conform to predetermined or target zones "Z" (FIG. 3A) in tissue "T" (e.g., in the cervix). The end effector electrode 50 may have a conical configuration.

Figure 3A:
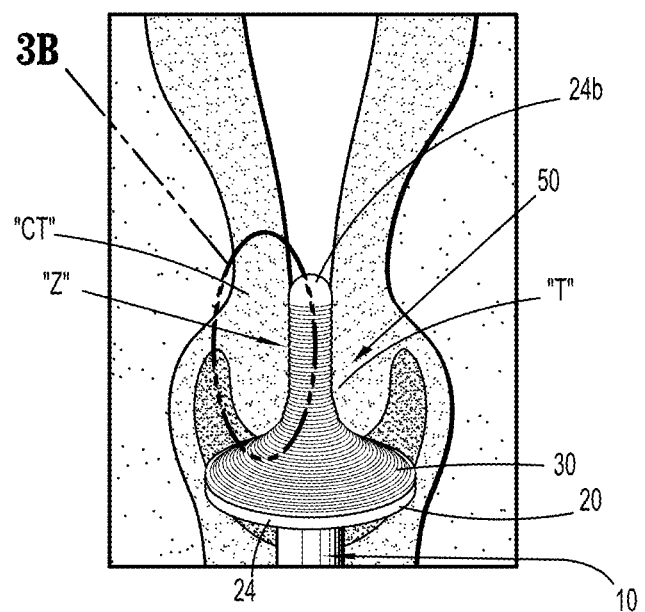
FIG. 3A is a perspective view illustrating the surface ablation system of FIG. 1 treating cervical tissue.

As seen in FIG. 3A, in use, the end effector electrode 50 is inserted into tissue "T," such as cervical tissue "CT" so that the circuit assembly 30 is positioned in contact with the cervical tissue "CT." Bipolar RF energy can then be activated so that the electrosurgical generator 40 transmits the energy through the traces 36 to treat the cervical tissue "CT." The procedure can be repeated as desired. The surface ablation system 10 can then be removed from the tissue "T."

Advantageously, the end effector electrode 50 is configured to be able to treat both irregular and regular cervix geometries. The end effector electrode 50 is also configured to provide treatment that penetrates tissue irregularities (e.g., crypts). With this end effector electrode 50, the total treatment time, including placement of the end effector electrode 50 can be less than 15 seconds and total treatment depth can be between about 0.5 mm to about 3 mm.

As can be appreciated relative to global treatment needs, this disclosure describes technology that can provide a complete but shallow (1 mm) treatment across an entire target area. The shape of the plug portion 24 of the surface ablation system 10 does not require dilation of the cervix. Further, with the surface ablation system 10 providing shallow treatment depths, only topical anesthetic may be needed for applying to the patient in connection with such treatment. The shallow treatment effect from the surface ablation system 10 enables a patient to recover quickly. Further, some patients may suffer from recurrence of cervical disease, but given the preservation of the cervical body proffered by treatment using the surface ablation system 10, the surface ablation system 10 can be utilized to perform a number of repeated treatments without causing preterm child birth.

Figure 3B:
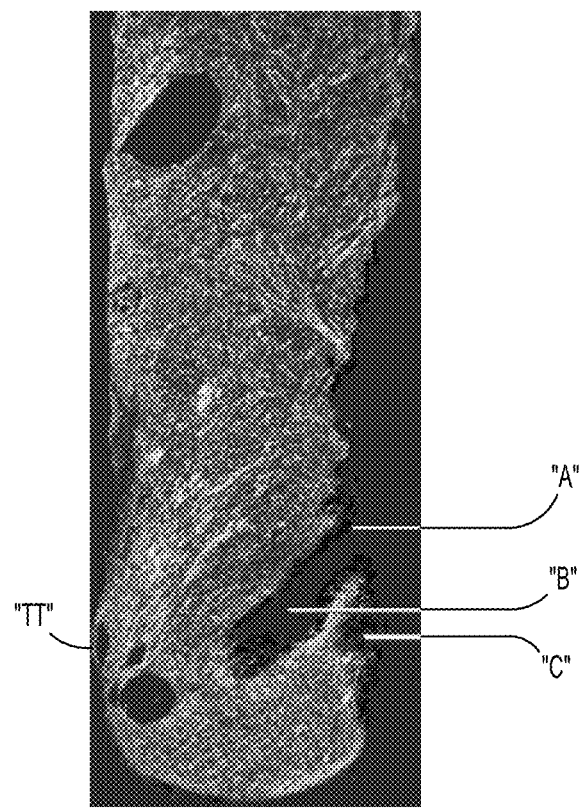
FIG. 3B is an enlarged view of a portion of the cervical tissue of the indicated area of detail shown in FIG. 3A after the cervical tissue was treated with the surface ablation system of FIG. 1.

With reference to FIG. 3B, a sample of treated cadaver tissue "TT" stained with picrosirius red shows denaturing of collagen typical of thermal damage, as indicated by reference "A," and which is present everywhere the end effector electrode 50 contacted during treatment. As indicated by reference "B," irregularities or crypts approximately 4 mm deep shows treatment to full depth. As indicated by reference "C," a region of deeper treatment is present where columnar epithelium forms a partial crypt. Such samples indicate that treatment is preferential toward destruction of the overlying epithelium (reference "C") likely due to the differential between conductivities of epithelium and the cervical body. Electrical current will be conducted into the crypts as the relative impedance of the tissue in direct contact with the electrode array desiccates first. The crypt with remain a highly conductive pathway and target heating zone. This greater conductivity of the crypt is possible due to a delayed heating of the epithelium and due to electrically conductive fluids and mucus contained in the crypt that are either naturally occurring or liberated fluid from the tissue in direct contact with the electrode array. Some necrosis may also be achieved by transfer of thermal energy contained in fluid and steam liberated from tissue in direct contact with the electrode array. This ability to destroy the epithelium in the crypts without full depth excision or necrosis of the cervical body is important for reducing general morbidity and may lower rates of preterm birth associated with conization while maintaining low recurrence.

Figure 4:
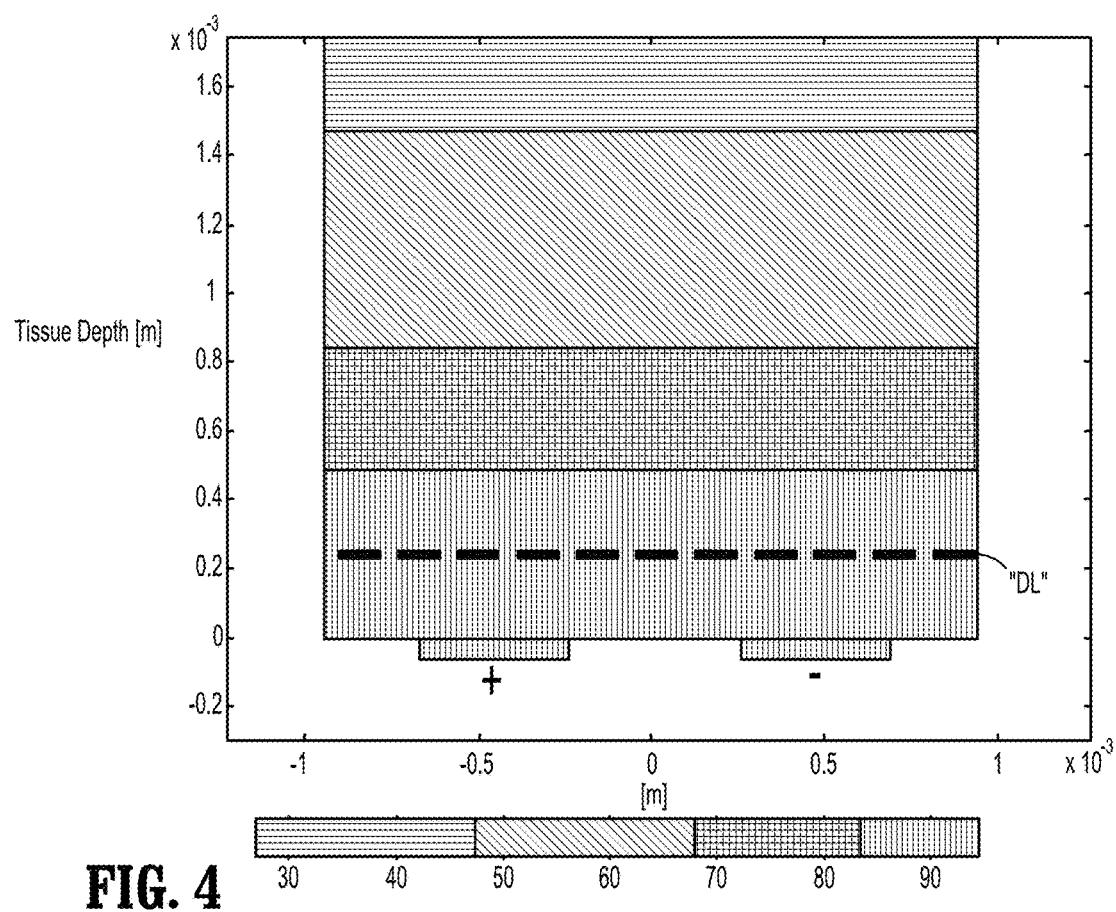
FIG. 4 is a simulated thermal chart for determining trace spacing for 1 mm treatment depth.

As seen in FIG. 4, an FEA simulation determined trace spacing necessary for 1 mm treatment depth. Based on the simulation, it was determined that coagulation necrosis is deeper than epithelium, but shallow enough preserve cervical patency. The simulation included thermal analysis using a model with two tissue layers representing columnar epithelium against the electrodes and the high-collagen body of the cervix above the dashed line "DL."

Figure 5A:
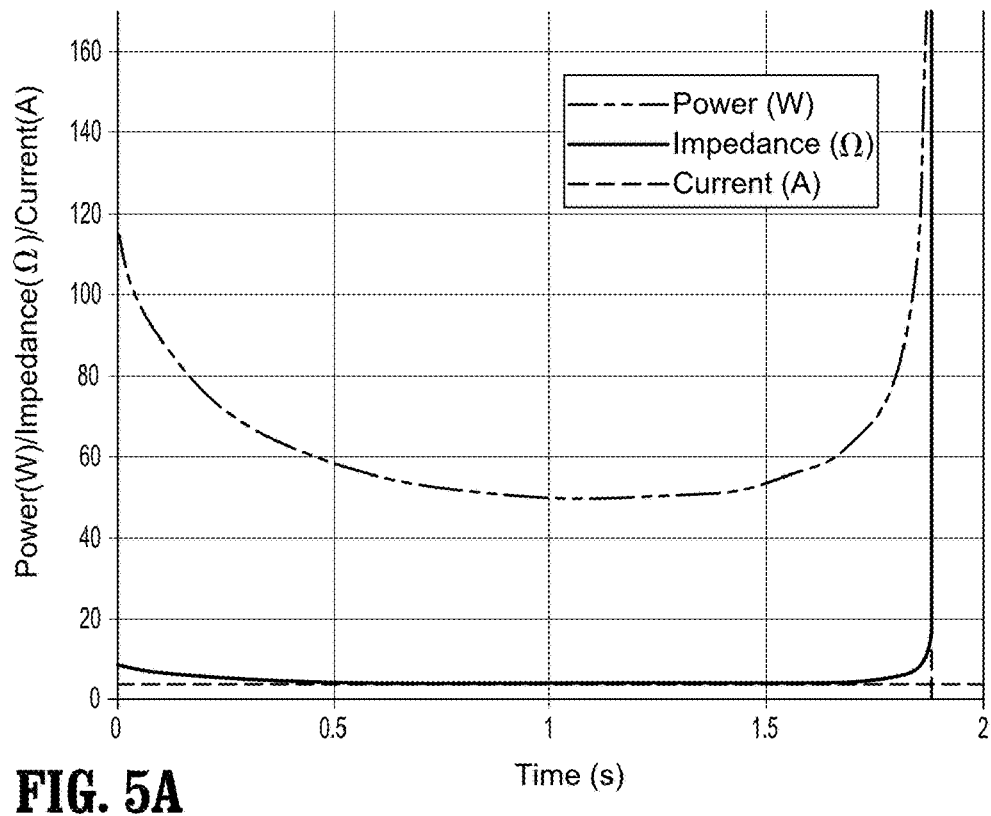
FIG. 5A is a chart of a simulated test for tissue impedance based on 4 amp activation.
Figure 5B:
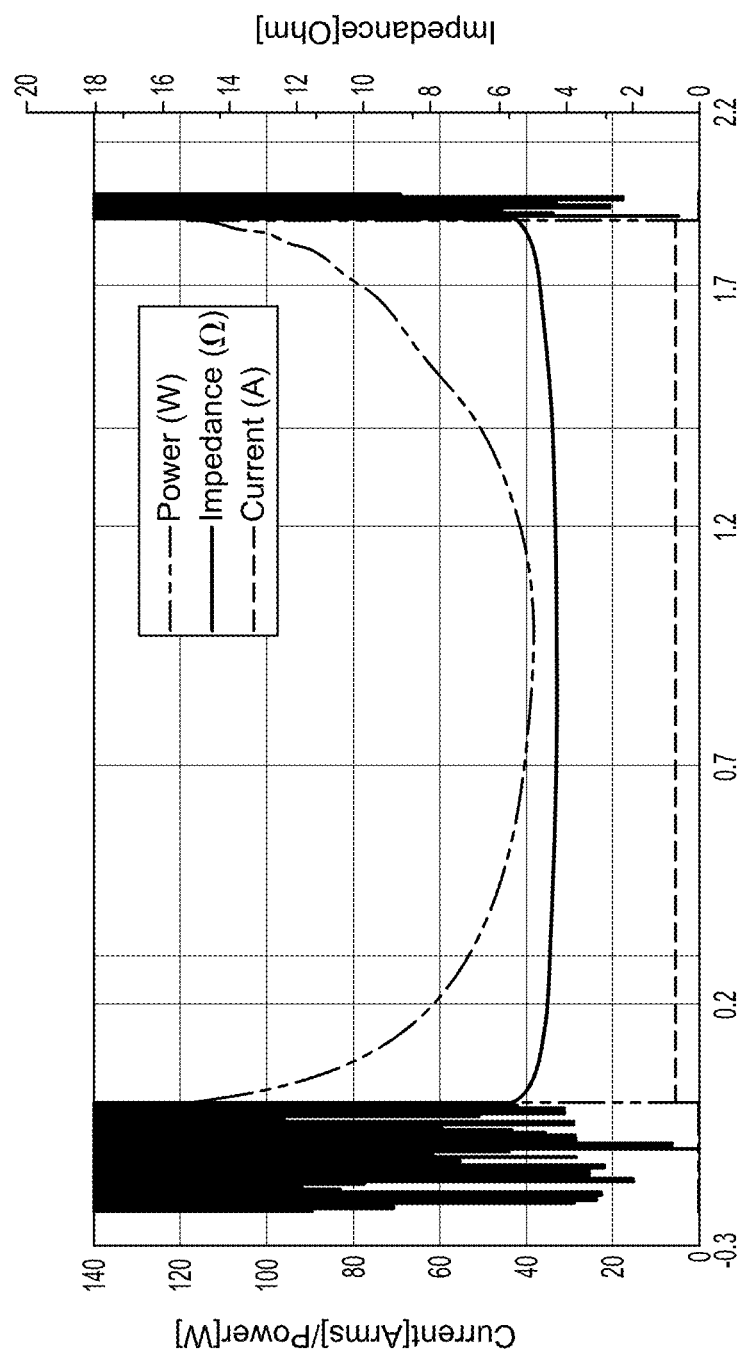
FIG. 5B is a chart of a bench test for tissue impedance based on 4 amp activation.
Figure 6:
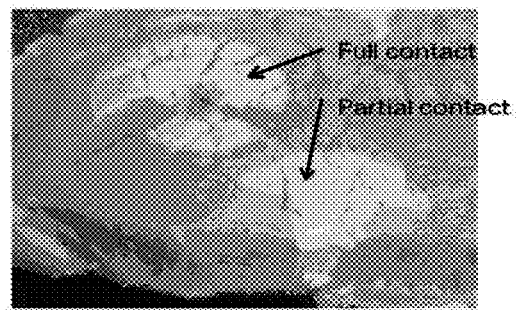
FIG. 6 is a perspective view of treated tissue from a bench test showing consistent effect with full and partial contact of an electrode of the surface ablation system of FIG. 1.

The charts of FIGS. 5A and 5B show simulated (FIG. 5A) and bench (FIG. 5B) tests of 4 amp activation. These charts indicate that impedance decreases as tissue warms and then increases as tissue desiccates. Thus, the surface ablation system 10 can be configured to include a power shut-off on impedance rise for consistent effect (rather than energy dosing the target). FIG. 6 illustrates a bench test showing the consistent effect with both full and partial contact of the end effector electrode.

Figure 7:
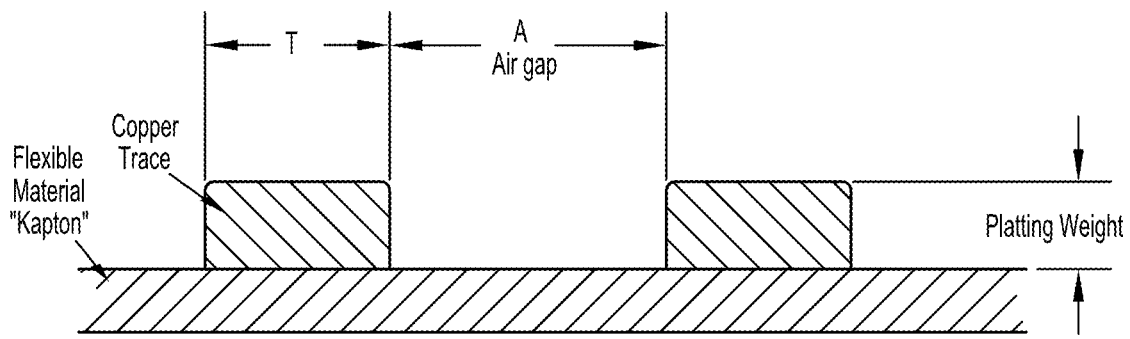
FIG. 7 is a cross-sectional view of a portion of an electrode trace arrangement of the surface ablation system of FIG. 1 illustrating electrode trace width and air gap width between adjacent electrode traces.
Figure 8:
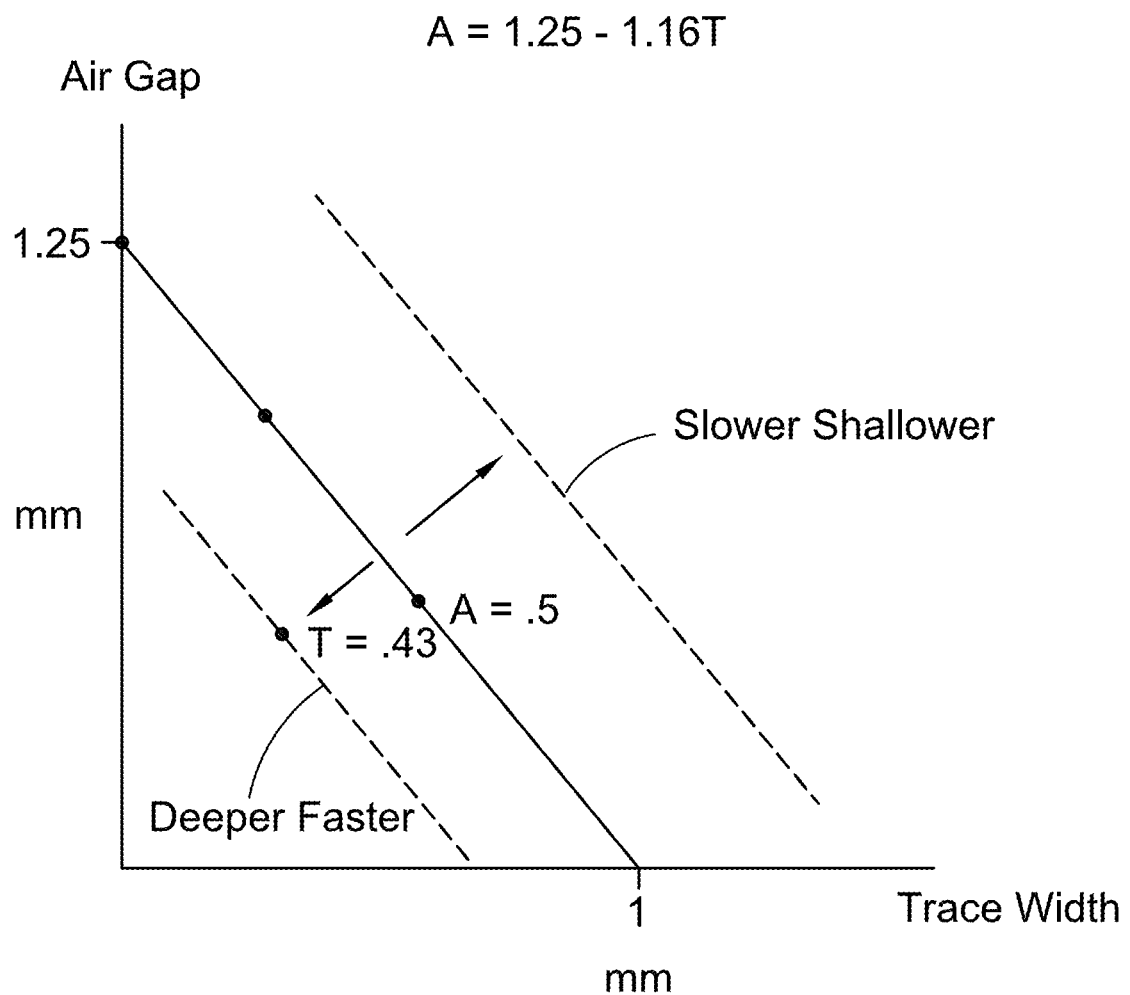
FIG. 8 is a graph illustrating air gap width versus electrode trace width.

FIG. 7 illustrates that the air gap width between adjacent traces is inversely proportional to the trace width of the respective electrode traces. In a practical simplification, the range of ablation depths possible with such configuration is defined by the relationship between the trace width and the air gap width for constant voltage and approximates the equation A=1.25-1.16T as shown in FIG. 8, where A is the air gap width and T is the trace width. In constant voltage, speed is optimized in a similar plot given that ablations with greater depth will reach an intermediate depth faster. For instance, with T=0.43 mm and A=0.5 mm, a slightly faster ablation will be provided while still reaching a 1-mm target depth as an intermediate point controlled by an impedance shutoff point. In some embodiments, the weight or thickness of the trace in FIG. 7 may be chosen simply as appropriate to carry the current needed by the surface volume of the electrode region.

Although described herein with respect to cervical tissue treatment, the surface ablation system 10 can be configured for use with any suitable procedure. For example, the ablation system 10 can be configured to treat endometriosis, stomach lesions, intestinal bleeding, skin lesions, etc.

As can be appreciated, securement of any of the components of the presently disclosed devices can be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A surface ablation system, comprising:
an electrosurgical generator;
an elongated shaft including a proximal end portion and a distal end portion;
a plug supported on the distal end portion of the elongated shaft, the plug including an annular flange at a proximal end thereof, a blunt tip at a distal end thereof, and a plug body disposed therebetween, the plug body including a first portion tapering distally from the annular flange to a second portion of constant outer diameter that extends between the first portion and the blunt tip; and
a circuit assembly supported on the plug and in electrical communication with the electrosurgical generator, the circuit assembly including a plurality of spaced-apart traces positioned in arrays about the plug, each of the traces configured to emit electrosurgical energy along the arrays to treat tissue positioned adjacent to the traces.

2. The surface ablation system according to claim 1, wherein the traces are positioned to achieve a specific depth of tissue thermal necrosis.

3. The surface ablation system according to claim 2, wherein the specific depth is about 1 mm.

4. The surface ablation system of claim 1, wherein the traces are configured to effectuate a secondary thermal necrosis in tissue irregularities not in direct contact with the traces.

5. The surface ablation system of claim 1, wherein the traces are axially spaced apart relative to a longitudinal axis defined through the elongated shaft and the plug.

6. The surface ablation system of claim 1, wherein the traces are uniformly spaced apart.

7. The surface ablation system of claim 1, wherein the circuit assembly is disposed on the plug body between the annular flange and the blunt tip such that the traces are distal to the annular flange and proximal to the blunt tip.

8. The surface ablation system of claim 1, wherein the circuit assembly includes at least one flex circuit mounted on the plug.

9. The surface ablation system of claim 1, wherein the circuit assembly includes a first flex circuit mounted on the second portion of the plug body and a second flex circuit mounted on the first portion of the plug body.

10. A method for effectuating surface ablation, the method comprising:

inserting an end effector electrode into tissue, the end effector electrode including a plug and a circuit assembly supported on the plug, the plug including an annular flange at a proximal end thereof, a blunt tip at a distal end thereof, and a plug body disposed therebetween, the plug body including a first portion tapering distally from the annular flange to a second portion of constant outer diameter that extends between the first portion and the blunt tip, the circuit assembly including a plurality of spaced-apart traces positioned in arrays about the plug;

conducting electrosurgical energy through the plurality of spaced-apart traces to ablate tissue; and effectuating secondary thermal necrosis in tissue irregularities not in direct contact with the traces.

11. The method of claim 10, wherein effectuating secondary thermal necrosis is achieved by one of:

electrical communication between traces adjacent to an electrically conductive tissue that lines the irregularities, electrical communication between the traces and fluid contained within the irregularities, transferred from a primary heating area as steam or thermally charged fluid from an electrode array contact area defined by the traces, or continued electrical driven effect through electrically conductive fluid discharged from a primary contact area into the irregularity.

12. The method of claim 10, further comprising causing power shutoff of the electrosurgical energy based on a sharp, sustained impedance rise following a previous minimum value.

* * * * *